United States Patent [19]

Skorianetz et al.

[11] 4,311,852

[45] Jan. 19, 1982

[54] OXYGEN CONTAINING DERIVATIVES OF TRICYCLO[6.2.1.0$^{2,7}$]UNDECANE

[75] Inventors: Werner Skorianetz, Dardagny; Günther Ohloff, Bernex, both of Switzerland

[73] Assignee: Firmenich SA, Geneva, Switzerland

[21] Appl. No.: 54,028

[22] Filed: Jul. 2, 1979

[30] Foreign Application Priority Data

Jul. 5, 1978 [CH] Switzerland ..................... 7320/78

[51] Int. Cl.$^3$ .................... C07C 69/013; C07C 69/06; C07C 69/07; C07C 69/14; C07C 69/145; C07C 69/54

[52] U.S. Cl. .............................. 560/256; 252/174.11; 252/522 R; 426/538; 426/650; 560/220; 568/373; 568/665; 568/817; 131/276

[58] Field of Search .................. 560/256, 220, 1, 129, 560/122–124; 568/817; 252/522 R

[56] References Cited

FOREIGN PATENT DOCUMENTS 1192527 5/1970 United Kingdom ................ 560/256
237886 12/1967 U.S.S.R. ............................. 560/256

*Primary Examiner*—Vivian Garner
*Attorney, Agent, or Firm*—Pennie & Edmonds

[57] ABSTRACT

New oxygen containing derivatives of tricyclo[6.2.1.0$^{2,7}$]undecane useful as perfuming or flavor-modifying ingredients in the manufacture of perfumes, perfumed articles, artificial flavors, foodstuffs, feedstuffs, beverages, pharmaceutical preparations or tobacco products.

Perfume or flavoring compositions containing same as organoleptically active ingredients.

4 Claims, No Drawings

OXYGEN CONTAINING DERIVATIVES OF TRICYCLO[6.2.1.0$^{2,7}$]UNDECANE

THE INVENTION

The invention refers to novel tricyclic compounds useful as perfuming or flavour-modifying ingredients, more precisely to compounds having the formula

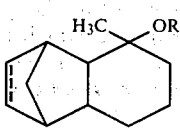

(I)

possessing a single or double bond in the position indicated by the dotted line and wherein symbol R represents either a hydrogen atom, or a saturated or unsaturated acyl radical containing from 1 to 6 carbon atoms.

The invention also refers to a method for modifying, improving or enhancing the organoleptic properties of perfumes, perfumed articles, artificial flavours, foodstuffs, feedstuffs, beverages, pharmaceutical preparations or tobacco products, which comprises adding thereto an effective amount of a compound of formula (I) as set forth hereinabove.

The invention finally refers to a perfume or flavour composition containing a compound of formula (I), as set forth hereinabove, as organoleptically active ingredient.

BACKGROUND OF THE INVENTION

Hitherto, natural products of vegetal or animal origin such as concretes, absolutes, balsams or essential oils for example have been widely used in the art of perfumery for the manufacture of perfumes. Due to the extensive use of perfumed products, cosmetics for example, in our modern society or to the perfuming of new materials, the consumption of such natural products is constantly increasing. The industry is therefore often confronted with the problems of scarcity or even disappearance of some of these natural products, essential oils in particular. In this respect one can cite essential oils such as clary sage oil (Salvia sclarea) or sweet marjoram oil (Origanum Majorana), both well appreciated and extensively used in modern perfumery, especially for "masculine" lines. The production of these rather expensive essential oils eminently depends on the climatic conditions, which conditions often vary from season to season. This means that the amounts produced may be sometimes drastically reduced and that the quality of the oil can vary from one harvest to the other.

It is therefore necessary for the perfume or flavour industry to have synthetically prepared chemical compounds able to reproduce, at least partially, some of the organoleptic effects of essential oils such as those mentioned hereinabove. Such chemical compounds would have the advantage to be prepared in practically unlimited amounts and to present a constant olfactive or gustative effect.

The object of the present invention precisely consists in providing the man in the art with a new class of odoriferous chemical compounds possessing useful organoleptic properties, namely enabling the man in the art to satisfactorily reproduce, in certain instances, some of the olfactive effects typical of clary sage oil or sweet marjoram oil.

This was quite surprising in view of the prior art which did not let one assume that such tricyclic chemical compounds would develop the olfactive characters defined hereinabove. On the contrary, the prior art teaches that the compound of formula

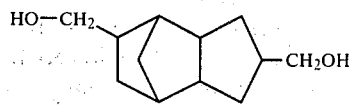

possesses a musky ordour—see DE-OS No. 23 07 627—, whereas compounds of formulae

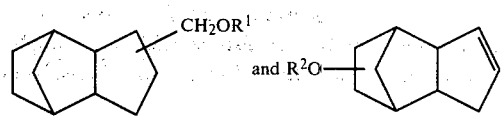

(R$^1$ = H, alkyl or acyl)     (R$^2$ = alkyl or alkenyl)

are characterized by their typically flowery, fruity and woody odour in the former case, and by their fruity, green and balsamic odour notes in the second case—see DE-OS Nos. 26 54 268 and 26 42 519, respectively.

The compound of formula

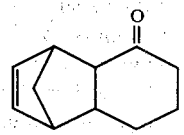

finally, is known in the art for its typically aromatic and "medicinal" odour note, reminiscent of that of wormwood (Artemisia absinthium) or liatris—see DE-OS No. 27 37 525.

PREFERRED EMBODIMENTS OF THE INVENTION

In formula (I) as defined hereinabove, symbol R may represent a hydrogen atom or an acyl radical such as formyl, acetyl, propionyl, butyryl, isobutyryl or acrylyl for example. Of particular interest are the following compounds: 3-methyl-tricyclo[6.2.1.0$^{2,7}$]undec-9-en-3-yl acetate, 3-methyl-tricyclo[6.2.1.0$^{2,7}$]undec-3-yl acetate and 3-methyl-tricyclo[6.2.1.0$^{2,7}$]undec-9-en-3-yl formate. More particularly, 3-methyl-tricyclo[6.2.1.0$^{2,7}$]undec-9-en-3-yl acetate having the formula

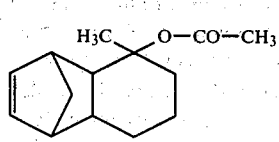

develops an original odour, at the same time fresh, green and natural, reminiscent of some of the olfactive effects of clary sage oil. The above compound is particularly useful as ingredient for preparing numerous perfume compositions, especially compositions of green, fresh, woody or chypre type for example. It was observed in particular that the addition of the above compound to "masculine" perfume compositions conferred thereto an original and lifting character.

The corresponding saturated derivative, viz, 3-methyl-tricyclo[6.2.1.0$^{2,7}$]undec-3-yl acetate presents the same features whereas 3-methyl-tricyclo[6.2.1.0$^{2,7}$]undec-9-en-3-yl formate develops moreover a typical woody, amber-like and aromatic odour note, reminiscent of that of sweet marjoram oil.

Compounds of formula (I) can be widely used, both in fine and technical perfumery, for instance for perfuming articles such as soaps, detergents, cosmetics or house-hold materials for example. For the preparation of perfume compositions, the most interesting odoriferous effects can be achieved by using proportions comprised between about 0.5 and 20% of the weight of the said composition. Proportions higher or lower than those given hereinabove may also be used, for example, when special effects are desired or for the preparation of perfume bases.

In the field of flavours, compounds of formula (I) are characterized by their green, woody and earthy flavour note, reminiscent of that of pine or vetiver oil, or of bornyl acetate. They can advantageously be used for preparing various artificial flavours or for the aromatization of foodstuffs, beverages, pharmaceutical preparations or tobacco products. For the preparation of flavouring compositions, the above compounds can be used in proportions of the order of about 0.5 to 5% of the weight of the said composition.

Compounds of formula (I) can be easily prepared from tricyclo[6.2.1.0$^{2,7}$]undec-9-en-3-one, after reaction thereof with methyl-magnesium chloride, bromide or iodide e.g., under the conditions of a Grignard reaction. The tertiary alcohol of formula

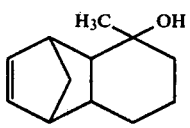

(Ia)

resulting from the above reaction is then converted into the corresponding ester according to the usual techniques, for example by treating it with a compound of formula

R—Y    (II)

wherein Y represents a halogen atom, chlorine or bromine, e.g., or an O-acetyl radical and R a saturated or unsaturated acyl radical containing from 1 to 6 carbon atoms. 3-Methyl-tricyclo[6.2.1.0$^{2,7}$]undec-9-en-3-yl formate, e.g., is prepared from the above alcohol (Ia), after treatment thereof with mixed formic-acetic anhydride [Y=O-acetyl; R=formyl in formula (II)]. In the same way the above alcohol can be converted into 3-methyl-tricyclo[6.2.1.0$^{2,7}$]undec-9-en-3-yl acetate by treating it with acetyl chloride [Y=Cl; R=acetyl in formula (II)].

The corresponding saturated esters can be prepared by directly hydrogenating the above cited compounds or by first hydrogenating alcohol (Ia) in the presence of a metal catalyst such as palladium on charcoal, Raney nickel or platinum oxide, e.g., to afford the compound of formula

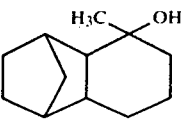

(Ib)

and subsequent esterification thereof as described hereinabove.

Tricyclo[6.2.1.0$^{2,7}$]undec-9-en-3-one used as starting material is a known compound which can be obtained from cyclohex-2-en-1-one and cyclopentadiene according to known methods (see: J. Org. Chem. 39, 3063 (1974) and DE-OS No. 27 37 525).

The following examples, wherein the temperatures are given in degrees centigrade and the abbreviations possess the usual meaning, are destined to illustrate the invention in a more detailed way.

EXAMPLE 1

3-Methyl-tricyclo[6.2.1.0$^{2,7}$]undec-9-en-3-ol

To a suspension of 4.55 g (0.187 mole) of magnesium turnings in 10 ml of anhydrous ether, there was added dropwise 28 g (0.197 mole) of methyl iodide in 50 ml of anhydrous ether. 26 g (0.160 mole) of tricyclo[6.2.1.0$^{2,7}$]undec-9-en-3-one in 150 ml of ether were then added to the above mixture, under vigorous stirring, the resulting reaction mixture being further refluxed for 24 hours. After cooling the mixture was then decomposed by the addition of 200 ml of 20% aqueous solution of NH$_4$Cl at 0°. The organic layer was then extracted with ether (3×50 ml), washed with water (3×50 ml), dried over Na$_2$SO$_4$ and finally evaporated to afford 27 g of crude material.

The thus obtained crude material was purified as follows: 27 g of said material were added to a mixture of 27 g of Girard P reagent, 27 ml of acetic acid and 270 ml of ethyl alcohol and then heated to reflux for 24 hours. After evaporation, the dry residue was diluted with 50 ml of water, extracted with ether (4×50 ml), successively washed with water (3×50 ml), Na$_2$HCO$_3$ 10% in water (3×50 ml) and finally water. After drying over Na$_2$SO$_4$, filtration, evaporation and distillation, there were isolated 14.7 g (51% yield) of the desired compound having b.p. 55°-60°/0.3 Torr.

IR: 3448, 2857, 1449, 1366, 1134, 1022, 816 cm$^{-1}$.

NMR: 1.2 (3H, s); 1.3-2.0 (8H, m); 2.0-3.0 (5H, m); 6.2 (2H, m) δ ppm.

MS: m/e=97 (13), 95 (90), 94 (17), 79 (18), 67 (16), 66 (100), 43 (20).

EXAMPLE 2

3-Methyl-tricyclo[6.2.1.0$^{2,7}$]undec-9-en-3-yl formate 13 g (0.127 mole) of acetic anhydride were first added under vigorous stirring and at 0° to 6 g (0.128 mole) of 98% aqueous formic acid, and the resulting mixture was then kept overnight at −5°.

7.4 g (0.042 mole) of 3-methyl-tricyclo[6.2.1.0$^{2,7}$]undec-9-en-3-ol—see Example 1—were then added to the above mixture, the whole mixture being stirred during 3 days at room temperature. The obtained mixture was then decomposed by the addition of 100 ml of a saturated aqueous solution of Na$_2$CO$_3$, extracted with ether (3×50 ml), washed with water (3×50 ml) and dried over Na$_2$SO$_4$. After evaporation there were obtained 8 g of crude material which by distillation at 0.02 Torr gave the desired compound in a 58% yield.

IR: 2910, 1714, 1440, 1236, 1170, 1115, 1020, 910, 895, 782 cm$^{-1}$.

NMR: 1.0–3.1 (12H, several m); 1.6 (3H, s); 6.12 (2H, m); 8.05 (1H, d) δ ppm.

MS: m/e=160 (11), 134 (9), 117 (8), 95 (100), 94 (71), 79 (53), 66 (86), 53 (7), 39 (13).

EXAMPLE 3

3-Methyl-tricyclo[6.2.1.0$^{2,7}$]undec-9-en-3-yl acetate 10 g (0.056 mole) of 3-methyl-tricyclo[6.2.1.0$^{2,7}$]undec-9-en-3-ol—see Example 1—were added to .77 g (0.636 mole) of N,N-dimethyl-anilin, 77 g (0.980 mole) of acetyl chloride and 400 ml of CHCl$_3$ and the obtained mixture was heated to reflux for 4 hours. After cooling to room temperature, the reaction mixture was poured onto crushed ice (300 ml) and the organic layer extracted with CH$_2$Cl$_2$ (3×100 ml). After washing with 10% aqueous HCl, neutralization with aqueous 10% NaHCO$_3$ and finally with water (3×50 ml), drying over Na$_2$SO$_4$ and evaporation, there were obtained 11.7 g of crude material. 6.8 g (55% yield) of the desired compound having b.p. 55°–60°/0.02 Torr were finally obtained by fractional distillation.

IR: 2915, 1724, 1570, 1449, 1362, 1239, 1117, 1022, 939, 897, 782 cm$^{-1}$.

NMR: 1.0–1.5 (5H, m); 1.5 (4H, s); 2.0 (4H, m); 2.1–3.0 (5H, m); 6.1 (2H, m) δ ppm.

MS: m/e=160 (17), 95 (100), 94 (88), 91 (17), 79 (64), 66 (82), 43 (46).

EXAMPLE 4

3-Methyl-tricyclo[6.2.1.0$^{2,7}$]undec-9-en-3-yl propionate 5 g (0.028 mole) of 3-methyl-tricyclo[2.6.1.0$^{2,7}$]undec-9-en-3-ol—see Example 1—and 47 g (0.50 mole) of propionyl chloride were reacted as indicated in Example 3 to afford, after extraction and evaporation, 6.5 g of crude material.

By distillation of the above material (b.p. 70°–75°/0.1 Torr), followed by purification by means of a column chromatography on silicagel (eluent cyclohexane/ether 7:3), 2.24 g (34% yield) of the desired compound were isolated. b.p. 65°–68°/0.1 Torr; m.p. ca. 30°

IR: 2882, 1712, 1449, 1333, 1181, 1114 cm$^{-1}$.

NMR: 1.08 (3H, t, J=7Hz); 1,53 (3H, s); 1.1–1.6 and 1.8–3.0 (14H); 6.03 (2H, m) δ ppm.

MS: m/e=125 (17), 95 (34), 81 (16), 73 (21), 55 (31), 43 (100).

EXAMPLE 5

3-Methyl-tricyclo[6.2.1.0$^{2,7}$]undec-9-en-3-yl acrylate 5 g (0.028 mole) of 3-methyl-tricyclo[6.2.1.0$^{2,7}$]undec-9-en-3-ol—see Example 1—and 46 g (0.50 mole) of acrylyl chloride were reacted as indicated in Example 3 to afford 7 g of crude material.

By distillation (b.p. 65°–67°/0.1 Torr) and purification by means of column chromatography on silicagel (eluent cyclohexane/ether 7:3), 1.9 g (29% yield) of the desired compound were isolated.

b.p. 68°–70°/0.1 Torr; m.p. 41°–42°

IR: 2899, 1704, 1613, 1443, 1395, 1198 cm$^{-1}$.

NMR: 1.1–3.1 (12H); 1.61 (3H, s); 5.56–6.53 (5H) δ ppm.

MS: m/e=160 (12), 95 (100), 94 (72), 79 (49), 66 (72), 55 (42).

EXAMPLE 6

3-Methyl-tricyclo[6.2.1.0$^{2,7}$]undec-9-en-3-yl isobutyrate 10 g (0.056 mole) of 3-methyl-tricyclo[6.2.1.0$^{2,7}$]undec-9-en-3-ol—see Example 1—and 7.5 g (0.070 mole) of isobutyryl chloride were reacted as indicated in Example 3 to afford, after extraction and distillation, 8 g of a material having b.p. 60°–85°/0.2 Torr.

By purification by means of column chromatography on silicagel (eluent cyclohexane/ethyl acetate 7:3), there were isolated 6 g (43% yield) of the desired compound.

IR: 2899, 1724, 1460, 1339, 1248, 1136, 1062, 913 cm$^{-1}$.

NMR: 1.0–1.2 (6H, 2s); 1.3–1.5 (6H, m); 1.6 (3H, s); 1.9–3.0 (7H, broad m); 6.1 (2H, m) δ ppm.

MS: m/e=160 (11), 95 (100), 94 (48), 79 (26), 66 (59), 43 (42).

EXAMPLE 7

3-Methyl-tricyclo[6.2.1.0$^{2,7}$]undecan-3-ol 25 g (0.140 mole) of 3-methyl-tricyclo[6.2.1.0$^{2,7}$]undec-9-en-3-ol—see Example 1—in 150 ml of methanol were hydrogenated under atmospheric pressure and at room temperature in the presence of 2.5 g of 10% palladium on charcoal. After filtration, evaporation and distillation (b.p. 60°–65°/0.1 Torr), there were isolated 24 g of a material containing ca. 90% of the desired compound according to vapour phase chromatographic analysis.

For its characterization, the above compound was further purified by means of a distillation on a spinning band column.

IR: 3484, 2857, 1449, 1357, 1121, 926 cm$^{-1}$.

NMR: 1.06 (1H, broad s); 1.22 (3H, s); 1.2–2.5 (16H) δ ppm.

MS: M$^+$=180 (23); m/e=162 (63), 134 (72), 95 (97), 79 (60), 71 (100), 43 (98).

EXAMPLE 8

3-Methyl-tricyclo[6.2.1.0$^{2,7}$]undec-3-yl formate 8.7 g of 3-methyl-tricyclo[6.2.1.0$^{2,7}$]undec-9-en-3-yl formate—crude material; see Example 2—in 60 ml of methanol were hydrogenated under atmospheric pressure and at room temperature in the presence of 0.8 g of 10% palladium on charcoal. After filtration and evaporation, the crude residue was extracted with ether (100 ml), washed with aqueous 10% NaHCO$_3$ (20 ml) and then with water to afford, after drying and evaporation, 8 g of crude material.

7 g of the above material were purified by means of column chromatography on silicagel (eluent cyclohexane/ether 7:3) to afford 2.2 g (25% yield) of the desired compound having b.p. 58°–60°/0.05 Torr.

IR: 2857, 1704, 1449, 1370, 1183, 1111 cm$^{-1}$.

NMR: 1.1–2.7 (16 H); 1.57 (3H, s); 8.1 (1H, broad s) δ ppm.

MS: m/e=162 (54), 134 (96), 119 (42), 95 (100), 79 (75), 67 (50), 41 (47).

EXAMPLE 9

3-Methyl-tricyclo[6.2.1.0$^{2,7}$]undec-3-yl acetate 22 g (0.122 mole) of 3-methyl-tricyclo[6.2.1.0$^{2,7}$]undecan-3-ol—see Example 7—and 220 ml of isopropenyl acetate were refluxed for 6 hours, in the presence of 0.1 g of p-toluenesulfonic acid. After cooling to room temperature, the reaction mixture was washed with aqueous 10% NaHCO₃ (30 ml), then with water (3×30 ml), dried over Na₂SO₄ and evaporated to afford 24 g of crude material.

After distillation (b.p. 55°–70°/0.05 Torr) of the above material in the presence of K₂CO₃, there were isolated 13 g (48% yield) of the desired compound.

IR: 2899, 1715, 1443, 1361, 1239, 1015 cm$^{-1}$.
NMR: 1.1–2.8 (16H); 1.52 (3H, s); 1.98 (3H, s) δ ppm.
MS: m/e = 162 (52), 134 (100), 119 (47), 106 (61), 95 (90), 79 (70), 43 (74).

EXAMPLE 10

The following three compounds were used as perfuming ingredients for the manufacture of toilet soaps as indicated hereinafter (parts by weight):

Compound A: 3-methyl-tricyclo[6.2.1.0$^{2,7}$]undec-9-en-3-yl acetate
Compound B: 3-methyl-tricyclo[6.2.1.0$^{2,7}$]undec-3-yl acetate
Compound C: 3-methyl-tricyclo[6.2.1.0$^{2,7}$]undec-9-en-3-yl formate

| Ingredients | Sample A | Sample B | Sample C |
| --- | --- | --- | --- |
| Commercial soap paste | 100 | 100 | 100 |
| Compound A | 1 | — | — |
| Compound B | — | 1 | — |
| Compound C | — | — | 1 |

The thus perfumed paste was then manufactured according to the usual techniques and the obtained perfumed samples were finally subjected to an olfactive evaluation which gave the following results:
Sample A: fresh, green and natural lifting odour; reminiscent of certain aspects of clary sage oil
Sample B: woody odour with amber-like and green notes; reminiscent of clary sage oil
Sample C: woody and amber-like odour with green and aromatic notes; reminiscent of sweet marjoram oil.

EXAMPLE 11

A perfumed detergent powder was prepared by intimately mixing the following ingredients (parts by weight);

| Ingredients | Sample A | Sample B | Sample C |
| --- | --- | --- | --- |
| Commercial detergent powder[1] | 100 | 100 | 100 |
| Compound A[2] | 0.15 | — | — |
| Compound B[2] | — | 0.15 | — |
| Compound C[2] | — | — | 0.15 |

[1]contains enzymes and perborates
[2]see Example 10

The thus perfumed samples were then subjected to an olfactive evaluation which gave the following results:
Sample A: pleasant green and fresh odour; reminiscent of clary sage
Sample B: slightly woody odour of green type with amber-like and aromatic notes
Sample C: woody and amber-like odour with green and aromatic notes; reminiscent of sweet marjoram.

It was further observed in the above three cases that the imparted odour remained unchanged after several weeks storage under the usual conditions. Moreover, it was apparent that towels treated with the perfumed detergent powder possessed a fragrance which perfectly stuck on the material after washing.

EXAMPLE 12

A perfumed shampoo was prepared by mixing the following ingredients (parts by weight):

| Ingredients | Sample A | Sample B | Sample C |
| --- | --- | --- | --- |
| Commercial shampoo base | 100 | 100 | 100 |
| Compound A[1] | 0.20 | — | — |
| Compound B[1] | — | 0.20 | — |
| Compound C[1] | — | — | 0.20 |

[1]see Example 10

The thus perfumed shampoos were then subjected to an olfactive evaluation which gave the following results:
Sample A: fresh and green lifting odour of "herbal shampoo" type
Sample B: slightly woody, green and amber-like odour; analogous to sample A
Sample C: woody, amber-like odour with green and aromatic notes; "medicinal"-like.

EXAMPLE 13

A perfume base for classical Eau de Cologne was prepared by mixing the following ingredients (parts by weight):

| Lemon oil | 250 |
| --- | --- |
| Bergamot oil | 300 |
| Orange oil | 150 |
| Petitgrain bigarade | 100 |
| Neroli bigarade | 20 |
| Lavender oil | 70 |
| Thyme oil | 10 |

After dilution of the above base at 3% in 95% ethyl alcohol there is obtained a classical Eau de Cologne with a warm and citrus-like odour.

By adding to 95 parts of the above Eau de Cologne 5 parts of a 10% solution of 3-methyl-tricyclo[6.2.1.0$^{2,7}$]undec-9-en-3-yl acetate in 95% ethyl alcohol, there was obtained a novel Eau de Cologne possessing a more lifting odour together with a pleasant "masculine" character.

An analogous effect was observed when, in the above example, 3-methyl-tricyclo[6.2.1.0$^{2,7}$]undec-9-en-3-yl acetate was replaced by 3-methyl-tricyclo[6.2.1.0$^{2,7}$]undec-3-yl acetate or 3-methyl-tricyclo[6.2.1.0$^{2,7}$]undec-9-en-3-yl formate.

EXAMPLE 14

A perfume base for masculine Eau du toilette was prepared by mixing the following ingredients (parts by weight):

| Linalyl acetate | 100 |
| --- | --- |
| Oak moss absolute 50%* | 80 |
| p-t-Butyl-cyclohexyl acetate | 70 |
| Lemon oil | 70 |
| Cedryl acetate | 60 |
| Orange oil of Florida | 50 |
| Lavender oil | 50 |
| Synthetic bergamot oil | 50 |
| Isobornyl acetate | 40 |
| EXALTEX®[1] | 40 |
| Ambrette musc | 30 |
| Oriental sandal wood oil | 60 |

| -continued | |
|---|---|
| Eugenol | 20 |
| Thyme oil 10%* | 20 |
| β-Damascenone 1%* | 20 |
| Neroli oil of Portugal | 10 |
| Coumarin | 10 |
| Lavender absolute | 10 |
| AMBROX ®[1] 1%* | 10 |
| Total | 800 |

*in diethyl phthalate
[1]origin: FIRMENICH SA, Geneva/Switzerland

The thus prepared base composition possesses an odour of "chypre" type.

By adding to 80 parts of the above base 20 parts of 3-methyl-tricyclo[6.2.1.0$^{2,7}$]undec-9-en-3-yl acetate there was obtained a novel perfume composition developing a fuller, rounder and more harmonious odour than that of the base.

An analogous effect was observed when, in the above example, 3-methyl-tricyclo[6.2.1.0$^{2,7}$]undec-9-en-3-yl acetate was replaced by 3-methyl-tricyclo[6.2.1.0$^{2,7}$]undec-3-yl acetate or 3-methyl-tricyclo[6.2.1.0$^{2,7}$]undec-9-en-3-yl formate. In this latter case moreover, the obtained perfume composition developed a pleasant woody and amber-like note.

What we claim is:

1. A compound of formula

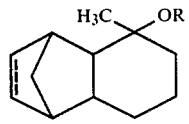

possessing a single or double bond in the position indicated by the dotted line and wherein symbol R represents either a hydrogen atom, or a saturated or unsaturated acyl radical containing from 1 to 6 carbon atoms.

2. 3-Methyl-tricyclo[6.2.1.0$^{2,7}$]undec-9-en-3-yl formate.

3. 3-Methyl-tricyclo[6.2.1.0$^{2,7}$]undec-9-en-3-yl acetate.

4. 3-Methyl-tricyclo[6.2.1.0$^{2,7}$]undec-3-yl acetate.

* * * * *